United States Patent
Short et al.

(10) Patent No.: US 9,946,796 B2
(45) Date of Patent: *Apr. 17, 2018

(54) PHENOTYPIC INTEGRATED SOCIAL SEARCH DATABASE AND METHOD

(71) Applicant: iPhenotype LLC, San Diego, CA (US)

(72) Inventors: Jay M. Short, Del Mar, CA (US); Steve Briggs, Del Mar, CA (US)

(73) Assignee: IPHENOTYPE LLC, San Diego, CA (US)

( * ) Notice: Subject to any disclaimer, the term of this patent is extended or adjusted under 35 U.S.C. 154(b) by 307 days.

This patent is subject to a terminal disclaimer.

(21) Appl. No.: 14/402,911

(22) PCT Filed: May 23, 2013

(86) PCT No.: PCT/US2013/042527
§ 371 (c)(1),
(2) Date: Nov. 21, 2014

(87) PCT Pub. No.: WO2013/177465
PCT Pub. Date: Nov. 28, 2013

(65) Prior Publication Data
US 2015/0112797 A1    Apr. 23, 2015

Related U.S. Application Data

(60) Provisional application No. 61/650,759, filed on May 23, 2012, provisional application No. 61/650,754, filed on May 23, 2012.

(51) Int. Cl.
| | | |
|---|---|---|
| G01N 33/53 | (2006.01) | |
| G06F 17/30 | (2006.01) | |
| G06F 19/24 | (2011.01) | |
| G06Q 30/02 | (2012.01) | |
| G06Q 50/22 | (2018.01) | |
| C12Q 1/68 | (2018.01) | |
| G06F 19/28 | (2011.01) | |

(52) U.S. Cl.
CPC ..... *G06F 17/30867* (2013.01); *C12Q 1/6883* (2013.01); *G06F 19/24* (2013.01); *G06Q 30/02* (2013.01); *G06Q 30/0251* (2013.01); *G06Q 50/22* (2013.01); *G16H 10/20* (2018.01); *C12Q 2600/158* (2013.01); *G06F 19/28* (2013.01)

(58) Field of Classification Search
None
See application file for complete search history.

(56) References Cited

U.S. PATENT DOCUMENTS

| | | | |
|---|---|---|---|
| 8,073,503 B2 | 12/2011 | Hoefel et al. | |
| 8,170,609 B2 | 5/2012 | Hedtke et al. | |
| 8,200,525 B2 | 6/2012 | Kilger et al. | |
| 9,316,651 B2 * | 4/2016 | Kalns | G01N 33/6848 |
| 2003/0004655 A1 | 1/2003 | Singh et al. | |
| 2007/0173726 A1 | 7/2007 | Kim et al. | |
| 2008/0033819 A1 | 2/2008 | Leschly | |
| 2008/0318624 A1 | 12/2008 | Hedtke et al. | |
| 2009/0117861 A1 | 5/2009 | Hoefel et al. | |
| 2009/0182625 A1 | 7/2009 | Kilger et al. | |
| 2010/0113891 A1 | 5/2010 | Kaput et al. | |
| 2011/0010099 A1 | 1/2011 | Adourian et al. | |
| 2012/0072233 A1 | 3/2012 | Hanlon et al. | |
| 2012/0130732 A1 | 5/2012 | Blander et al. | |
| 2012/0302843 A1 | 11/2012 | Otsubo et al. | |

FOREIGN PATENT DOCUMENTS

| | | |
|---|---|---|
| CN | 1543317 A | 11/2004 |
| JP | 2006516338 A | 6/2006 |
| JP | 2009128178 A | 6/2009 |
| JP | 2011067708 A | 4/2011 |
| JP | 2011209871 A | 10/2011 |
| JP | 2013008159 A | 1/2013 |
| KR | 101132260 B1 | 4/2012 |
| WO | WO2003070745 A2 | 8/2003 |
| WO | WO2004042511 A2 | 5/2004 |

OTHER PUBLICATIONS

2012 Bristol Stool Test.*
Al-Ashkar et al. (Cleveland Clinic Journal of Medicine 2003, vol. 70, p. 866-881).*
CINGA Biometric Screening (2010).*
Chinese Office Action; dated Sep. 6, 2016 for CN Application No. CN201380027116.8.
International Search Report; dated Sep. 6, 2013 for PCT Application No. PCT/US2013/042527.
European Search Report; dated Dec. 1, 2015 for EP Application No. EP13794462.5.
Australian Examination Report; dated Sep. 4, 2017 for AU Application No. AU2013266193.
Chinese Office Action; dated May 9, 2017 for CN Application No. CN201380027116.8; including an English abstract.

(Continued)

*Primary Examiner* — Changhwa J Cheu
(74) *Attorney, Agent, or Firm* — Mendelsohn Dunleavy, P.C.

(57) ABSTRACT

The present invention provides methods, databases and devices for establishing the first integration of social behavior with biological phenotypic measurements. In one embodiment, a method for correlating data from a sample database and a survey database is provided. The method comprises obtaining a sample comprising biological molecules from an individual, simultaneously obtaining survey data from the individual, storing the survey data in the survey database, analyzing the sample of biological molecules to determine the composition of biological molecules, storing the data from the composition in the sample database, and correlating the data from the sample database to the data from the survey database.

10 Claims, No Drawings

(56) References Cited

OTHER PUBLICATIONS

Japanese Office Action; dated Jun. 6, 2017 for JP Application No. JP2015514207.
Chinese Decision on Rejection; dated Jan. 8, 2018 for CN Application No. 201380027116.8.
European Search Report; dated Jan. 3, 2018 for EP Application No. 14800690.1.

* cited by examiner

PHENOTYPIC INTEGRATED SOCIAL SEARCH DATABASE AND METHOD

The present invention provides methods, databases and devices for establishing the first integration of social behavior with biological phenotypic measurements.

It is widely acknowledged that searching data is valuable for the sorting and correlation of information. With the abundance of data available to search, methods to decrease the error rate of data searching, and increase the efficiency and speed of data searching are highly desirable. Useful results can depend on query inputs and correlations employed. Several groups have used user answers to questions to correlate preferences for products and activities, and beliefs (for example, Hunch: www.hunch.com), or behavior shopping as a guide to recommend future product purchases (Amazon). Other specialized programs ("apps") for devices include software that measure and compare data to like users for future prediction, for example restaurant apps, where users rate restaurants and data is collected and used in prediction of future restaurant choices.

Methods of predicting consumer behavior have also been described. For example, U.S. Pat. No. 8,200,525 (incorporated herein by reference) describes a process and system for predicting consumer behavior by combining converted information from disparate databases.

The ability to predict future choices is highly desirable. For example the ability to predict future choices provides such benefits as allowing sellers to be able to locate highly targeted consumers during a purchase cycle. With the right information, merchants can achieve customized, targeted advertising and offer incentives to customers (discount coupons). It is also widely recognized that consumers desire to identify via search exactly what they want quickly, easily and with mobile devices. Making searches more efficient also engages and provides users with significant added value. Traditionally, there are no quantitative physical biological component inputs in any of these examples.

Several groups have, however, used genetic fragments such as single-nucleotide polymorphism (SNPs or DNA sequence variation that occur when a single nucleotide—A, T, C or G—in the genome or other shared sequence differs between members of a biological species or paired chromosomes in an individual) and online questionnaires to correlate health risks in individuals, as well as to determine genealogy of individuals (for example, 23 and Me, National Geographic and WorldFamilies.net). Further, many companies use genetic information to diagnose disease, including mental conditions.

Examples of measurement of biological components to diagnose medical conditions include tests such as the widely available pregnancy tests and other over the counter assays available to consumers and medical laboratories; yet these examples do not specifically describe or predict behavior, a feature that is desirable for merchants and consumers.

The present invention provides a novel method of integrating social search with biological phenotype, and a database of such information for use by merchants, consumers and others. In the methods and databases of the present invention, correlation is made between phenotypes (biological phenotypes and behavioral or emotional phenotypes), versus the traditional approach of correlating genotype to phenotype or genotype to genotype.

Databases are collections of data, and can be stored in on or more devices configured to process data, such as a computer.

The term phenotype, as used hereunder, includes traits or characteristics that can be made visible by some technical procedure, and can include behavior as an observable characteristic. Phenotypes are constrained by quantifiable genetic, developmental and environmental variables, which can be measured as biomolecular states, such as genome sequence, epigenomic modifications, RNA and microRNA levels, protein levels, protein folding and modifications, metabolite levels and electrical signals. A phenotype is the composite of an organism's observable characteristics or traits: such as its morphology, development, biochemical or physiological properties, phonology, behavior, and products of behavior (such as a bird's nest). Phenotypes result from the expression of an organism's genes as well as the influence of environmental factors and the interactions between the two. In the methods of the present invention, biomolecular states are measured using genetic, developmental and/or environmental or other variables, such as those described herein.

The specific state of the proteome (the entire set of proteins expressed by a genome, cell, tissue or organism) in a given cell, tissue, or organism is known as the proteotype. The proteotype is the proteomic state that uniquely underlies a phenotype. Proteotyping mines the potential genetic information of a gene at the protein level by visualizing unique amino acid signatures; many protein forms resulting from a single gene are visualized. The proteotype integrates constraints imposed by the genotype, the environment, and by developmental history (i.e., a skin cell has a different proteotype than a heart cell with the same genotype in the same environment). The proteotype can directly determine phenotype since all molecules are made by and regulated by proteins. Thus, the proteotype can be used to directly infer genotype contributions to phenotype (because peptides map to DNA), and enables a synthetic reconstruction of phenotype (changes in protein levels or in post-translational modifications can be engineered). A complete description of the proteotype can define a phenotype at the molecular level.

It is recognized that activities and actions of an organism are affected by proteins. Proteins can be measured to demonstrate the biomolecular state of an individual. The large-scale study of proteins, "proteomics", is currently used to diagnose disease and to determine if a gene is expressed in a sample. In the past, more deficient methods were employed to determine protein related activities, for example nucleic acid (RNA) levels were measured. Proteomics can be more accurate for certain studies concerning protein related activity than determining, for example, RNA levels, since transcription rates, RNA half-life, protein half-life, protein distribution all impact whether a protein is available at a sufficient level to allow a protein related activity to occur. While nucleic acid contributes to protein levels by encoding a protein and thereby allowing a protein to be expressed, whether a protein is actually present and in sufficient quantity is determine by a myriad of factors. Thus, measuring proteins is an optimal way to decrease error and reduce misinterpretation of correlations. In an embodiment of the present invention, proteomics and/or proteotyping is utilized to measure the biomolecular state of an individual, or biological phenotype of an individual. Methods of purifying proteins from samples, and measuring proteins, including high throughput analysis of proteomes (for example, by mass spectrometry), are widely used and known in the art. Such methods are useful in the methods of the present invention.

It is further recognized that other biological molecules, such as peptides, metabolites, hormones and small molecules, affect and/or indicate activities and behavior of an organism. For example, the female reproductive hormone oxytocin has been correlated to generous and caring behavior. Quantitative physical biological component inputs of the present invention can include measurement or description of DNA type, RNA levels, microRNA types or levels, protein levels, proteotype, metabolic levels or even qualitative or quantitative MRI. In another embodiment of the present invention, measurement of biological molecules, such as peptides, hormones and/or small molecules, or any combination thereof, is performed to measure the biomolecular state of an individual.

In the methods of the present invention, biological molecules, such as proteins, are identified that are markers for emotional or behavioral states of individuals. Emotional states include, but are not limited to, basic emotions such as feeling tenderness, or being excited, happy, sad, angry or scared. After and during collection of data, including data about the presence or absence of the biological molecule(s) and data from the behavioral or emotional state of the individual, the data is integrated and analyzed. Data that is determined to correlate the phenotypes (for example, bias data) is retained and data not correlating phenotypes is eliminated. The data is stored, and a database is created. Collection of data can continue, and best correlations can be rank ordered with the best data retained and the lowest correlations optionally eliminated over time. The methods reveal an empirical correlation of biological molecules, or state, to a behavioral or emotional state.

The term "sample" as used herein means bodily fluid or cells, including but not limited to saliva, sweat, blood, tears, mucus, urine, stool, mouth cell scrapings, stool, hair follicle, fingernails or other bodily cells. Samples can be collected by an individual breathing onto a surface, scraping a check, spitting into a tube, urinating into a on onto a container or surface, or providing a liquid sample in any other method whereby the sample can be collected for analysis, for example using a device. It is contemplated that computer chips can be utilized to directly analyze, or present samples to a device (for example, a computer) that will analyze the sample. For example, nanotechnology has been used to create devices for testing disease states. Body gases have been measured on a devise using carbon nanotube sensor technology to diagnose disease. For example, nucleic acids are immobilized on a detection chip, individuals expose chips to body gas(es), nucleic acids bind variably to nucleic acid sequences on the chip resulting in unique patterns after detection, and the presence or absence of gas is correlated to disease. Proteins have also been coupled with carbon nanotube transistors, and the resulting devices transduce signals associated with protein binding events, providing a general method for the study of protein function using electronic readout in a nanotube format. These represent examples of methods to collect and analyze samples in the methods of the present invention.

The term "assay", as used herein, is a measurement to quantify or qualify a component of a sample, preferably a protein, peptide, hormone, or other biological molecule. In the method of the present invention, one or more proteins and/or the entire proteome of cells in a sample from an individual is assayed. It is contemplated that an individual can deliver a sample, or the data from the assay of a sample to a location where it can be used in a correlation. Initially, one or more proteins, and/or the entire proteome will be assayed. In a preferred embodiment, one protein is assayed, for example a hormone, for example adrenaline. In another embodiment, 5 proteins are assayed. In another embodiment 10 proteins are assayed. In another embodiment, 50 proteins are assayed. In another embodiment 100 proteins are assayed. In another embodiment, 500 proteins are assayed. In another embodiment 1000 proteins are assayed. In another embodiment, 2000 proteins are assayed. In another embodiment 2500 proteins are assayed. In another embodiment, 3000 proteins are assayed. Proteins that are always present or always absent are predictive of future behavior since their presence or absence correlates with the response to query, as set forth herein. Further, proteins that are induced upon a response further, allow genetic association, which allows DNA to be predictive (however, it is recognized that the gene that encodes the protein is not necessarily the gene inducing the particular protein level shift).

In one aspect of the present invention, after proteins are measured in a sample, genes encoding such proteins can be determined. It is then possible to use a surrogate nucleic acid (such as DNA or RNA) assay to measure the biomolecular state of the individual. The reverse process of measuring proteins first, followed by use of nucleic acid as a surrogate for determination of a biomolecular state of an individual, has not been pursued at scale. One reason may be the belief that nucleic acid measurement is optimal for determining the biomolecular state of an individual, and another reason may be the higher cost of protein assays versus nucleic acid assays. Thus, in another embodiment of the present invention, proteins are first measured, followed by determination of corresponding DNA or RNA molecules, and such nucleic acid molecules are then assayed to measure the biomolecular state of an individual.

In another embodiment of the present invention, physiological states are measured for correlation, such as heart rate, galvanic response, body temperature, pupil dilation or other physiological characteristics.

Measured biomolecular states are then correlated with behavioral states of individuals, for example social behavior, to yield database(s) (one or more collection(s) of related data organized for convenient access, preferably in a computer) of information about individuals that are useful for a variety of purposes, including use by merchants in the prediction of buying behavior or to provide new information to users about their existing and potential future preferences.

In one aspect of the present invention, along with the biomolecular state of individuals, the behavioral states of individuals are measured with queries to establish and evolve a database of information. Individuals, or individuals knowledgeable about another individuals behavior, will complete a behavioral questionnaire or series of questions designed to indicate or evaluate feeling, behavior, preferences, mood, sensation, senses, or other physical, biological, emotional, psychological, or mental states. For example, questions can be "Do you like riding motorcycles?", "Do you get nauseated on roller coasters?", "Are you married?", "Are you happy?", "Are you a republican?", "which texture do you prefer (show a picture)?", "do you prefer a hot climate or a cool climate?", "do you prefer the color red or the color yellow?", "Do you like to drive fast?" and/or other such questions whereby answers indicate individual preferences, feelings, behavior or other state. Information can be gathered about likes and dislikes in the form of visual presentations as well. For example, pictures can be shown to individuals and comments given by the individual regarding opinion, such as "I see it and I like it", "I see it and I don't like it," "I haven't seen it, but I will like it," "I haven't seen it, but I won't like it". Thus a phenotype is established side-by-side with the behavioral state of an individual; such information allows the correlation of a phenotype with a behavioral state, facilitating the ability to predict future behavior when a phenotype is present. The larger the database, the more desirable, since the more information linking phenotype to behavior creates more accuracy in the prediction.

Thus, in the method of the present invention answers from the behavioral questionnaire, or series of behavior questions, are then correlated with the phenotype results from the assay. Proteomic analysis can be performed on a number of individuals emotional states, e.g. perhaps 5, 10, 20 25 or 100 people per emotional state, initially to establish the database. Data is collected, and a database is generated which correlates phenotype results from the assay with behavior from the answers to the questions. Over time, the database can be modified to eliminate behavioral data not correlated with phenotype. Data can be continually collected, and the database evolved. Behavior to phenotype matches can be ranked, and ranking can modify, or evolve, over time as new information is input into the database. It is contemplated that new behavior information and phenotype information can be continually integrated into the database.

Many examples of data collection and storage for analysis exist. For example, HLA typing databases collect and store for information purposes information about the HLA type of individuals.

In the method of the present invention, decision making and data search results are linked to a user biological phenotype to yield information and patterns that are useful in a variety of applications. This biological integration into data search can contribute to lowering the high error rate of search efficiency and speed. The marker used to measure the biomolecular state of the individual, such as proteins, that are always present or always absent can be predictive of future behavior since their presence or absence will be correlated with the responses to questions.

In one method of the present invention, phenotypic assessment is fundamental for correlation to behavior in order to derive a valid "emotype", or a temporal biologic condition or state correlated with behavior and feeling, that allows assessment and prediction of current and future behavior.

Thus, the present invention represents a method for correlating data from a sample database and a survey database comprising: obtaining a sample comprising biological molecules from an individual, simultaneously obtaining survey data from the individual; storing the survey data in a survey database; analyzing the sample of biological molecules to determine the composition of biological molecules; storing the data from the composition in a sample database; correlating the data from the sample database to the data from the survey database. In another embodiment, the present invention is a method for predicting consumer behavior comprising: using a processing device; obtaining a sample comprising biological molecules from a consumer; simultaneously obtaining survey data from the consumer; storing the survey data in a survey database; analyzing the sample of biological molecules to determine the composition of biological molecules; storing the data from the composition in a sample database; correlating the data from the sample database to the data from the survey database; using the correlated data to predict consumer behavior using the processing device. In yet another embodiment, the present invention is a method for predicting an individual's behavior or preferences, the method comprising: obtaining a sample comprising biological molecules from an individual, simultaneously obtaining survey data from the individual; storing the survey data in a survey database; analyzing the sample of biological molecules to determine the composition of biological molecules; storing the data from the composition in a sample database; correlating the data from the sample database to the data from the survey database; predicting behavior or preference based on the correlation between the biological data in the sample database and the survey data in the survey database. In yet another embodiment, the present invention is a method for predicting an individual's behavior or preferences, the method comprising: obtaining a sample comprising biological molecules from an individual; analyzing the sample of biological molecules to determine the composition of biological molecules; correlating the data from the sample to the data from a survey database; predicting behavior or preference based on the correlation between the biological data in the sample and the survey data in the survey database. In another embodiment, the present invention is a method for correlating data from a previously generated sample database and a previously generated survey database comprising: correlating data from the sample database to the data from the survey database. In another embodiment, the present invention is a method for correlating data from a sample database and a survey database comprising: obtaining a sample comprising biological molecules from an individual, analyzing the sample of biological molecules to determine the composition of biological molecules; correlating the data from the sample database to the data from a survey database. In another embodiment, the present invention is a method for predicting one or more individual's behavior or preferences, the method comprising: obtaining samples comprising biological molecules from one or more individuals; analyzing the samples of biological molecules to determine the composition of biological molecules; storing the data from the composition in a sample database; correlating the data from the sample database to the data from a survey database; predicting behavior or preference based on the correlation between the biological data in the sample database and the survey data in the survey database.

Individuals include consumers in the methods of the present invention. Databases include information from a plurality of individuals.

The methods of the present invention are useful in the several applications where demonstration or prediction of the affinity of individuals for anything (for example people, electronic gadgets, music, food, fashion, games, books, and consumables, and the like) is useful. For example dating services, the pet services and supply industry (pets biomolecular state can be measured and owners, for example, can provide information about behavior states), the political system (to provide information about voting choices), the travel industry (marketing for vacation locations) will find the information provided by the database correlating biomolecular states with individuals behavior (for example, choices).

The following references are incorporated entirely herein by reference:

De Ruiter, J. R. (2004) 'Genetic markers in primate studies: elucidating behaviour and its evolution.', International journal of primatology, 25 (5). pp. 1173-1189.

Publication entitled: Opportunities in Neuroscience for Future Army Applications (2009) Board on Army Science and Technology (BAST), Committee on Opportunities in Neuroscience for Future Army Applications; Division on Engineering and Physical Sciences; NATIONAL RESEARCH COUNCIL OF THE NATIONAL ACADEMIES, THE NATIONAL ACADEMIES PRESS, Washington, D.C.☐www.nap.edu Goldsmith et al., Vol. 5 ' No. 7 ' 5408-5416 ' 2011, ACS Nano; Published online Jun. 22, 2011.

Samuel M. Khamis, et al., Homo-DNA Functionalized Carbon Nanotube Chemical Sensors, Journal of Physics and Chemistry of Solids 71 (2010) 476-479.

S. M. Khamis, et al., DNA-decorated carbon nanotube-based FETs as ultrasensitive chemical sensors: Discrimination of homologues, structural isomers, and optical isomers, AIP Advances 2, 022110 (2012); doi: 10.1063/1.4705394

Yian-Biao Zhang, et al., Functionalized Carbon Nanotubes for Detecting Viral Proteins, Nano Letters, 2007 Vol. 7, No. 10 3086-3091

Without further elaboration, it is believed that one skilled in the art can, using the preceding description, utilize the present invention to its fullest extent.

What is claimed is:

1. A method for correlating composition data from a sample database and survey data from a survey database comprising:

obtaining samples comprising biological molecules of protein from a plurality of individuals, obtaining a plurality of sets of survey data from the plurality of individuals, wherein each said set of survey data is obtained for one of the plurality of individuals simultaneously with one of the samples obtained from the same individual;

storing the plurality of sets of survey data obtained from the plurality of individuals in the survey database;

analyzing the biological molecules in the samples obtained from the plurality of individuals to determine the composition of biological molecules to generate composition data;

storing the composition data in the sample database; and correlating the composition data from the sample database to the survey data from the survey database, wherein the survey data comprises answers to questions about each of the plurality of individuals' consumer behavior, purchase preferences, mood, senses, sensation, mental state, psychological state, physical state and emotional state, the samples are selected from the group consisting of urine, stool, blood, the individual's breath, human cells, hair, fingernails, saliva, mucus, and tears, and the correlating step generates a correlation suitable for predicting consumer behavior for use by merchants in the prediction of buying behavior or to provide new information to users about their existing and potential future purchases.

2. The method of claim 1 wherein the biological molecules further comprise at least one of a small molecule, a metabolite, a peptide, a hormone, and a nucleic acid.

3. The method of claim 1 wherein the individual is a consumer.

4. The method of claim 1 wherein the analyzing step is performed using a mass spectrometer.

5. The method of claim 1 wherein the survey data comprises data from a physiological measurement.

6. The method of claim 5 wherein the physiological measurement is selected from the group consisting of heart rate, galvanic response, body temperature, and pupil dilation.

7. The method of claim 1 wherein the survey data is generated by persons familiar with the individuals.

8. The method of claim 1, wherein the individuals are consumers, and the predicting step comprises using the correlations to predict consumer behavior using a processing device.

9. The method of claim 8 wherein the processing device is a computer.

10. The method of claim 8 wherein the processing device is a mobile phone.

* * * * *